United States Patent [19]

Toyoshima et al.

[11] 4,267,172
[45] May 12, 1981

[54] BIS(TRIORGANOSILYLALKYL) PHOSPHITES

[75] Inventors: Shigeshi Toyoshima, Funabashi; Ryuichi Sato, Urawa; Koichi Ito, Higashi Kurume; Toshio Shinohara; Masatoshi Arai, both of Annaka, all of Japan

[73] Assignee: Shin-Etsu Chemical Co. Ltd., Tokyo, Japan

[21] Appl. No.: 78,772

[22] Filed: Sep. 25, 1979

[30] Foreign Application Priority Data

Sep. 26, 1978 [JP] Japan .............................. 53-118491

[51] Int. Cl.$^3$ ..................... A01N 55/00; C07F 9/02; C07F 7/08
[52] U.S. Cl. ..................................... 424/184; 556/404
[58] Field of Search .............. 260/448.2 N; 424/184; 556/404

[56] References Cited

U.S. PATENT DOCUMENTS

| | | | |
|---|---|---|---|
| 2,864,845 | 12/1958 | Kerschner et al. | 556/404 |
| 3,898,257 | 8/1975 | Gregory | 556/404 X |
| 4,089,884 | 5/1978 | Shinohara et al. | 260/448.2 N |

*Primary Examiner*—Paul F. Shaver
*Attorney, Agent, or Firm*—Toren, McGeady and Stanger

[57] ABSTRACT

The present invention presents a novel class of compounds bis(triorganosilylalkyl) phosphites, e.g. bis(trimethylsilylmethyl) phosphite. The compound is readily prepared by the reaction of a corresponding triorganosilyl alkanol with phosphorus trichloride or by the partial hydrolysis of a corresponding tris(triorganosilylalkyl) phosphite with an equimolar amount of water followed by distillation of the reaction mixture.

The compound has a remarkable anti-transplanted tumor effectiveness as established by the test with mice as the test animals for preventing the growth of Ehrlich's cancer cells and Sarcoma 180 cells. The compound has very low toxicity when orally administrated.

15 Claims, No Drawings

BIS(TRIORGANOSILYLALKYL) PHOSPHITES

BACKGROUND OF THE INVENTION

The present invention relates to bis(triorganosilylalkyl)phosphites as a novel class of organosilicon compounds and the method for the preparation thereof as well as to a novel medicament containing a bis(triorganosilylalkyl)phosphite as the therapeutically effective ingredient.

Recently, a patent has been issued which discloses tris(triorganosilylalkyl) phosphites as a novel class of organosilicon compounds (see U.S. Pat. No. 4,089,884) and a method for the preparation of these tris phosphite compounds but corresponding bis phosphite compounds have been unknown as described in no prior art literatures.

As is well known, efforts are being directed in these days to the establishment of a novel medicament containing an organosilicon compound as the therapeutically effective ingredient utilizing the unique properties thereof hitherto not expected in any ordinary organic compounds. In particular, extensive investigations have been undertaken to develop an organosilicon compound which is effective as an antihypertensive agent or as an anti-transplanted tumor agent and several organosilicon compounds are proposed. These oerganosilicon compounds are, however, not formulated practically due to the undesirable side reactions with their relatively strong toxicity. Therefore, it is an important problem in the recent pharmacological research works to establish a novel antihypertensive or anti-transplanted tumor agent containing an organosilicon compound with less toxicity as its therapeutically effective ingredient.

SUMMARY OF THE INVENTION

An object of the present invention is to provide a bis(triorganosilylalkyl) phosphite which is a novel organosilicon compound.

Another object of the present invention is to provide a novel method for the preparation of a bis(triorganosilylalkyl) phosphite.

Further object of the present invention is to provide a novel medicament containing a bis(triorganosilylalkyl) phosphite as the therapeutically effective ingredient thereof.

The bis(triorganosilylalkyl) phosphites of the present invention are represented by the general formula $$[R_3Si(CH_2)_nO]_2POH,$$

where R is a monovalent hydrocarbon group having from 1 to 6 carbon atoms and n is a number of 1, 2 or 3.

The bis(triorganosilylalkyl) phosphite is prepared by the reaction of a corresponding triorganosilyl alkanol with phosphorus trichloride or, alternatively, by the partial hydrolysis of a corresponding tris(triorganosilylalkyl) phosphite with a limited amount of water.

The bis(triorganosilylalkyl) phosphite, e.g. bis(trimethylsilylmethyl) phosphite, is effective as an anti-transplanted tumor agent as is clearly demonstrated by the tests with mice as the test animals with its very low acute toxicity as low as 1200 mg/kg of the safety dose level by oral administration.

DETAILED DESCRIPTION OF THE PREFERRED EMBODIMENTS

In the above given general formula representing the inventive bis(triorganosilylalkyl) phosphites, R is a hydrocarbon group having from 1 to 6 carbon atoms as exemplified by alkyl groups such as methyl, ethyl, propyl,-butyl and the like, alkenyl groups such as vinyl and allyl groups and aryl groups such as phenyl group. The hydrocarbon groups R in a molecule can be either of one and the same kind or of different kinds. The symbol n in the general formula denotes a number of 1, 2 or 3 so that the triorganosilylalkyl groups can be either one of triorganosilylmethyl, -ethyl and -propyl groups, of which the compounds with n=2 are somewhat unstable.

Thus, several of the examples of the inventive bis(triorganosilylalkyl) phosphites in conformity with the above given general formula and the definitions of the symbols include bis(trimethylsilylmethyl) phosphite, bis(trimethylsilylpropyl) phosphite, bis(dimethyl-n-butylsilylmethyl) phosphite, bis(dimethylphenylsilylmethyl) phosphite, bis(dimethyl-n-butylsilylpropyl) phosphite and the like.

The bis(triorganosilylalkyl) phosphites of the present invention can be readily prepared in two different synthetical procedures as described below.

The first of the synthetical methods is the reaction of a corresponding triorganosilyl alkanol with phosphorus trichloride according to the following equation $$3R_3Si(CH_2)_nOH + PCl_3 \rightarrow [R_3Si(CH_2)_nO]_2POH + 2HCl + R_3Si(CH_2)_nCl,$$

where R and n each have the same meaning as defined above.

The second alternative method for the preparation of the bis(triorganosilylalkyl) phosphite is the partial hydrolysis of a corresponding tris(triorganosilylalkyl) phosphite with a stoichiometric amount of water according to the following equation, $$[R_3Si(CH_2)_nO]_3P + H_2O \rightarrow [R_3Si(CH_2)_nO]_2POH + R_3Si(CH_2)_nOH.$$

In practicing the above first method, phosphorus trichloride is added dropwise into the triorganosilyl alkanol so that the reaction proceeds readily and smoothly with evolution of hydrogen chloride which is eliminated from the reaction mixture. It should be noted that, as is taught by the disclosure in U.S. Pat. No. 4,089,884, the reaction of the triorganosilyl alkanol and phosphorus trichloride proceeds to form a corresponding tris(triorganosilylalkyl) phosphite if the reaction is carried out in the presence of a trialkylamine as an acceptor for hydrogen chloride. The presence of such an acid acceptor is rather undesirable in this case and the reaction is carried out at a temperature in the range from −20° to +150° C. or, more preferably, from 0° to 70° C. in most cases. The amount of the trialkylsilyl alkanol is preferably more than 3 times of the phosphorus trichloride by moles. After completion of the reaction, the resultant reaction mixture is subjected to distillation under a reduced pressure to give the desired bis(triorganosilylalkyl) phosphite.

The reaction of the above first method can be performed without the use of an organic solvent but it is optional, if necessary, to use a solvent such as an aromatic hydrocarbon solvent, e.g. benzene or toluene, and an aliphatic hydrocarbon solvent, e.g. hexane or octane, as well as other inert solvents such as diethyl ether and dibutyl ether.

The above given second method is a partial hydrolysis of a tris(triorganosilylalkyl) phosphite with an equimolar amount of water and the latter is added dropwise into the former to effect the reaction almost quantitatively. The amount of water may not be exactly equimolar but a small excess of water can be used without particular disadvantages. The reaction is an exothermic reaction and the reaction can proceed at room temperature with evolution of heat of reaction so that the temperature of the reaction mixture is increased from room temperature to 50° to 60° C. or higher. The reaction of the partial hydrolysis is almost complete within about 30 to 60 minutes and the resultant reaction mixture is subjected to distillation under a reduced pressure to give the objective bis(triorganosilylalkyl) phosphite.

The bis(triorganosilylalkyl) phosphite thus obtained are novel compounds not described in any prior art literatures. The compounds are useful as a flame retardant agent when incorporated in articles fabricated with various thermoplastic resins. The compounds are also useful as a reagent for several organic synthetic reactions as described below with a similar reactivity to that of an ordinary alkyl phosphite. In the following reaction equations, the symbols R and n each have the same meaning as defined before and R' and X denote a monovalent organic group and a halogen atom, respectively.

(a) Michaelis-Beggar reaction:

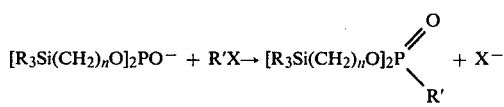

(b) Michael-type addition reaction:

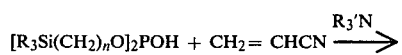

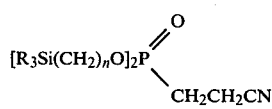

(c) Addition reaction to carbonyl groups:

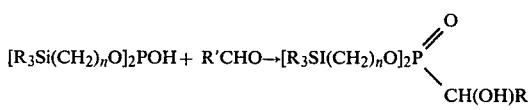

Another important application of the inventive bis(triorganosilylalkyl) phosphites is as a therapeutically effective ingredient in medicaments such as an anittransplanted tumor agent. The toxicity of the inventive compounds is very low as has been established by the animal test in so far as the acute toxicity concerns so that there is practically no need to take into consideration the acute toxicity of the compound by oral administration.

Following are the examples to describe the synthesis and identification of the inventive compounds in further detail as well as to illustrate the low toxicity of the compounds and the effectiveness of the compounds as an anti-transplanted tumor agent demonstrated by the animal test with mice as the test animals.

EXAMPLE 1

Into 67.7 g (0.650 mole) of trimethylsilylmethyl alcohol contained in a reaction vessel of 100 ml capacity equipped with a stirrer, a thermometer and a reflux condenser was added dropwise 27.5 g (0.200 mole) of phosphorus trichloride with agitation over a period of 30 minutes followed by heating at 100° C. for 2 hours, during which hydrogen chloride gas was evolved and discharged out of the reaction vessel. After completion of the reaction, the resultant reaction mixture was subjected to distillation under a reduced pressure to give 23.3 g of a clear, colorless liquid boiling at 78°–79° C./1.0 mmHg.

The liquid product thus obtained was examined by elementary analysis, infrared absorption spectral analysis and NMR absorption spectral analysis to give the results as given below, together with the value of the refractive index from which the product was identified to be the objective bis(trimethylsilylmethyl) phosphite $[(CH_3)_3SiCH_2O]_2POH$. The above given yield of the product was 45.4% of the theoretical.

Elementary analysis:

|  | Si | C | H | O | P |
|---|---|---|---|---|---|
| Found, % | 21.98 | 37.81 | 9.08 | 18.75 | 12.19 |
| Calculated as $C_8H_{23}O_3Si_2P$, % | 22.08 | 37.77 | 9.11 | 18.87 | 12.17 |

NMR absorption spectral analysis:

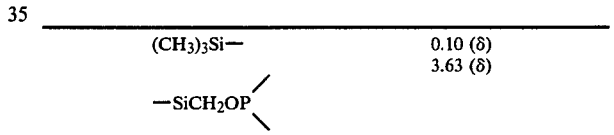

Infrared absorption spectral analysis:

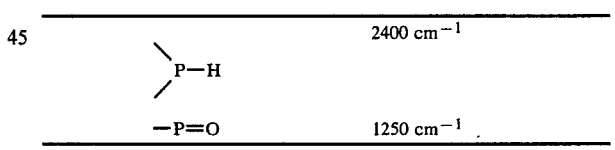

Refractive index: $n_D^{25}$ 1.4330.

EXAMPLE 2

Into 50 g (0.147 mole) of tris(trimethylsilylmethyl) phosphite contained in a reaction vessel as in Example 1 was added dropwise 2.60 g (0.144 mole) of water over a period of 10 minutes. During the period, the temperature of the reaction mixture was increased from 20° C. to 52° C. After cooling of the reaction mixture to room temperature where agitation was continued for further one hour, the reaction mixture was subjected to distillation under a reduced pressure to give 35.5 g of a clear, colorless liquid boiling at 78°–79° C./1.0 mmHg. The elementary analysis, NMR absorption spectral analysis, infrared absorption spectral analysis and measurement of the refractive index undertaken with this product gave identical results as with the product in Example 1. The above given yield of the objective bis(trimethylsilylmethyl) phosphite corresponds to 94.2% of the theoretical.

EXAMPLE 3

The reaction procedure was substantially the same as in Example 2 and 4.2 g (0.233 mole) of water was added dropwise into 100 g (0.235 mole) of tris(trimethylsilylpropyl) phosphite with agitation. After completion of the reaction and cooling of the reaction mixture to room temperature, the reaction mixture was subjected to distillation under a reduced pressure to give 70.0 g of a clear, colorless liquid boiling at 133°–134° C./1.0 mmHg.

The elementary analysis, NMR absorption spectral analysis and infrared absorption spectral analysis as well as determination of the refractive index undertaken with this liquid product gave the results shown below, from which the product was identified to be the objective bis(trimethylsilylpropyl) phosphite [$(CH_3)_3Si(CH_2)_3O]_2POH$. The above given yield of the reaction product corresponds to 95.9% of the theoretical.

Elementary analysis:

|  | Si | C | H | O | P |
| --- | --- | --- | --- | --- | --- |
| Found, % | 18.16 | 46.40 | 10.01 | 15.49 | 9.89 |
| Calculated as $C_{12}H_{31}O_3Si_2P$, % | 18.09 | 46.41 | 10.06 | 15.46 | 9.98 |

NMR absorption spectral analysis:

| $(CH_3)_3Si-$ | 0.04 (δ) |
| --- | --- |
| $-CH_2-O-P\diagup\diagdown$ | 3.83 (δ) |

Infrared absorption spectral analysis:

| $\diagdown P-H \diagup$ | 2400 cm$^{-1}$ |
| --- | --- |
| $-P=O$ | 1250 cm$^{-1}$ |

Refractive index: $n_D^{25}$ 1.4398.

EXAMPLE 4

The reaction procedure was substantially the same as in Example 2 and 3.80 g (0.211 mole) of water was added dropwise into 100 g (0.244 mole) of tris(dimethyl-n-butylsilylmethyl) phosphite with agitation and the reaction mixture after completion of the reaction was subjected to distillation under a reduced pressure to give 71.4 g of a clear, colorless liquid product boiling at 132°–133° C./1.0 mmHg.

The elementary analysis, NMR absorption spectral analysis, infrared absorption spectral analysis and determination of the refractive index undertaken with this liquid product gave following results, from which the product was identified to be the objective bis(dimethyl-n-butylsilylmethyl) phosphite [$(CH_3)_2(n-C_4H_9)SiCH_2O]_2POH$. The above given yield of the product corresponds to 93.5% of the theoretical.

Elementary analysis:

|  | Si | C | H | O | P |
| --- | --- | --- | --- | --- | --- |
| Found, % | 16.54 | 19.68 | 10.42 | 14.22 | 9.16 |
| Calculated as $C_{14}H_{35}O_3Si_2P$, % | 16.59 | 49.66 | 10.42 | 14.18 | 9.15 |

NMR absorption spectral analysis:

| $(CH_3)Si-$ | 0.05 (δ) |
| --- | --- |
| $-CH_2-O-P\diagup\diagdown$ | 3.60 (δ) |

Infrared absorption spectral analysis:

| $\diagdown P-H \diagup$ | 2400 cm$^{-1}$ |
| --- | --- |
| $-P=O$ | 1250 cm$^{-1}$ |

Refractive index: $n_D^{25}$ 1.4455.

EXAMPLE 5

The reaction procedure was substantially the same as in Example 1 and 21 g (0.153 mole) of phosphorus trichloride was added dropwise into 85 g (0.487 mole) of dimethyl-n-butylsilylpropyl alcohol. Distillation of the reaction mixture after completion of the reaction under a reduced pressure gave 60.3 g of a clear, colorless liquid product boiling at 163°–164° C./1.0 mmHg.

The elementary analysis, infrared absorption spectral analysis and determination of the refractive index undertaken with this liquid product gave following results, from which the product was identified to be the objective bis(dimethyl-n-butylsilylpropyl) phosphite [$(CH_3)_2(n-C_4H_9)-Si(CH_2)_3O]_2POH$. The above given yield of the product corresponds to 96.9% of the theoretical.

Elementary analysis:

|  | Si | C | H | O | P |
| --- | --- | --- | --- | --- | --- |
| Found, % | 14.20 | 54.77 | 10.95 | 12.18 | 7.81 |
| Calculated as $C_{18}H_{43}O_3Si_2P$, % | 14.23 | 54.78 | 10.98 | 12.16 | 7.85 |

Infrared absorption spectral analysis:

| $\diagdown P-H \diagup$ | 2400 cm$^{-1}$ |
| --- | --- |
| $-P=O$ | 1250 cm$^{-1}$ |

Refractive index: $n_D^{25}$ 1.4519.

EXAMPLE 6

The reaction procedure was substantially the same as in Example 2 and 1.5 g (0.0833 mole) of water was added dropwise into 45 g (0.0873 mole) of tris(dimethylphenylsilylmethyl) phosphite with agitation. Distillation of the reaction mixture after completion of the reaction under a reduced pressure gave 16.6 g of a clear, colorless liquid product boiling at 180°–182° C./1.0 mmHg.

The elementary analysis, NMR absorption spectral analysis, infrared absorption spectral analysis and determination of the refractive index undertaken with this liquid product gave following results, from which the product was identified to be the objective bis(dimethylphenylsilylmethyl) phosphite $[(CH_3)_2(C_6H_5)SiCH_2O]_2POH$. The above given yield of the product corresponds to 52.8% of the theoretical.

Elementary analysis:

|  | Si | C | H | O | P |
|---|---|---|---|---|---|
| Found, % | 14.88 | 57.13 | 7.15 | 12.67 | 8.17 |
| Calculated as $C_{16}H_{27}O_3Si_2P$, % | 14.84 | 57.11 | 7.19 | 12.68 | 8.18 |

NMR absorption spectral analysis:

| $(CH_3)Si-$ | 0.29 (δ) |
| 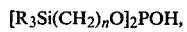 | 7.20 (δ) |

Infrared absorption spectral analysis:

|  | 2400 cm$^{-1}$ |
| $-P=O$ | 1250 cm$^{-1}$ |

Refractive index: $n_D^{25}$ 1.5230.

EXAMPLE 7

The acute toxicity of bis(trimethylsilylmethyl) phosphite as one of the inventive compounds was examined by oral administration to mice as the test animals. Thus, the compound was dissolved in olive oil in a concentration of 5% by weight and the solution was administrated orally to mice belonging to groups each composed of 20 mice with a body weight of each 20 to 40 g in a dose of 300 mg/kg or 600 mg/kg calculated as the compound per se. None of the mice indicated any symptom of intoxication. When the dose was increased to 1200 mg/kg, some of the mice exhibited lowered spontaneous activity but none of the mice died by poisoning.

The above results of oral administration test led to a conclusion that the safety level of dose of the compound is at least 1200 mg/kg in so far as the acute toxicity concerns.

EXAMPLE 8

Ehrlich's cancer cells of $5=10^6$ in number were transplanted subcutaneously to the back of each of 12 ICR(CD-1) mice having a body weight of 20 to 22 g each. Beginning with the second day from the transplantation, bis(trimethylsilylmethyl) phosphite was administrated by intraperitoneal injection in a dose of 100 mg/kg every two days to each of the 6 mice of the above 12 mice until the 20th day and the mice were killed on the 21st day to examine the weight of the cancer cells.

One of the 6 mice of the test group died during the period and the average weight of the cancer cells in the surviving 5 mice was 0.307±0.3027 g while the average weight of the cancer cells in the surviving 5 mice of the 6 mice belonging to the control group was 1.616±1.0445 g on the 21st day clearly indicating the effectiveness of the inventive compound as an anti-transplanted tumor agent.

EXAMPLE 9

Sarcoma 180 cells of $4.5 \times 10^6$ in number were transplanted subcutaneously to the back of each of 20 ICR(CD-1) mice having a body weight of 20 to 22 g each. Beginning with the second day from the transplantation, bis(trimethylsilylmethyl) phosphite was administrated intraperitoneally in a dose of 100 mg/kg every two days to each of the 7 mice of the above 20 mice as the test group. The mice were killed on the 21st day and the weight of the Sarcoma 180 cells was examined to find that the average weight of the cells in the surviving 6 mice was 3.218±3.3851 g while the average weight of the Sarcoma 180 cells in the surviving 7 mice of the 13 mice belonging to the control group was 4.117±2.2652 g clearly indicating the effectiveness of the compound as an anti-transplanted tumor agent.

What is claimed is:

1. A bis(triorganosilylalkyl) phosphite represented by the general formula $[R_3Si(CH_2)_nO]_2POH$, where R is a monovalent hydrocarbon group having from 1 to 6 carbon atoms and n is a number of 1, 2 or 3.

2. The bis(triorganosilylalkyl) phosphite as claimed in claim 1 wherein the group represented by R is an alkyl group selected from the class consisting of methyl, ethyl, propyl and butyl groups.

3. The bis(triorganosilylalkyl) phosphite as claimed in claim 1 wherein the group represented by R is phenyl group.

4. Bis(trimethylsilylmethyl) phosphite.
5. Bis(trimethylsilylpropyl) phosphite.
6. Bis(dimethyl-n-butylsilylmethyl) phosphite.
7. Bis(dimethyl-n-butylsilylpropyl) phosphite.
8. Bis(dimethylphenylsilylmethyl) phosphite.
9. A method for the preparation of a bis(triorganosilylalkyl) phosphite which comprises reacting a triorganosilyl alkanol represented by the general formula $R_3Si(CH_2)_nOH$, where R is a monovalent hydrocarbon group having from 1 to 6 carbon atoms and n is a number of 1, 2 or 3, with phosphorus trichloride.

10. The method as claimed in claim 9 wherein the reaction is carried out in the absence of an acceptor for hydrogen chloride.

11. The method as claimed in claim 9 or claim 10 wherein the amount of the triorganosilyl alkanol is about 3 times of the phosphorus trichloride by moles.

12. A method for the preparation of a bis(triorganosilylalkyl) phosphite which comprises partially hydrolyzing a tris(triorganosilyl) phosphite represented by the general formula $[R_3Si(CH_2)_nO]_3P$, where R is a monovalent hydrocarbon group having from 1 to 6 carbon atoms and n is a number of 1, 2 or 3, with water.

13. The method as claimed in claim 12 wherein the amount of water is approximately equal to the amount of the tris(triorganosilylalkyl) phosphite by moles.

14. An anti-transplanted tumor medicament containing an effective amount of a bis(triorganosilylalkyl) phosphite as a therapeutically effective ingredient thereof and a carrier.

15. The medicament as claimed in claim 14 wherein the bis(triorganosilylalkyl) phosphite is bis(trimethylsilylmethyl) phosphite.

* * * * *